US011604161B2

United States Patent
Niizuma et al.

(10) Patent No.: US 11,604,161 B2
(45) Date of Patent: Mar. 14, 2023

(54) GAS SENSOR

(71) Applicant: NGK INSULATORS, LTD., Aichi (JP)

(72) Inventors: Shotaro Niizuma, Kasugai (JP); Yusuke Watanabe, Nagoya (JP); Toshihiro Hirakawa, Kasugai (JP); Hayami Aota, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 77 days.

(21) Appl. No.: 17/093,676

(22) Filed: Nov. 10, 2020

(65) Prior Publication Data

US 2021/0140916 A1   May 13, 2021

(30) Foreign Application Priority Data

Nov. 12, 2019  (JP) .............................. JP2019-204527

(51) Int. Cl.
*G01N 27/407* (2006.01)
*G01N 27/406* (2006.01)
*G01N 33/00* (2006.01)
*G01N 27/41* (2006.01)
*G01N 27/409* (2006.01)

(52) U.S. Cl.
CPC ....... *G01N 27/4077* (2013.01); *G01N 27/409* (2013.01); *G01N 27/4062* (2013.01); *G01N 27/4071* (2013.01); *G01N 27/4078* (2013.01); *G01N 27/41* (2013.01); *G01N 33/0037* (2013.01); *G01N 33/0067* (2013.01)

(58) Field of Classification Search
CPC ........... G01N 27/4077; G01N 27/4062; G01N 27/4071; G01N 27/4078; G01N 27/409; G01N 27/41; G01N 33/0037; G01N 33/0067; Y02A 50/20
See application file for complete search history.

(56) References Cited

U.S. PATENT DOCUMENTS

| 8,398,837 B2 * | 3/2013 | Matsui | G01N 27/4062 204/426 |
| 10,031,047 B2 * | 7/2018 | Oba | G01N 27/4062 |
| 2003/0024300 A1 * | 2/2003 | Kojima | G01N 27/4077 73/31.05 |

(Continued)

FOREIGN PATENT DOCUMENTS

| EP | 899562 A2 * | 3/1999 | .......... G01N 27/407 |
| EP | 1524518 A1 * | 4/2005 | .......... G01N 27/407 |
| JP | 2018-105661 A | 7/2018 | |

*Primary Examiner* — Joshua L Allen
*Assistant Examiner* — Shizhi Qian
(74) *Attorney, Agent, or Firm* — Mattingly & Malur, PC

(57) ABSTRACT

A gas sensor includes a sensor element, an elastic insulating member, a plurality of lead wires, a plurality of metal terminals, and a ceramic housing. The plurality of lead wires are inserted in the elastic insulating member. The plurality of metal terminals each have a first end electrically connected to the sensor element, and a second end electrically connected to a corresponding one of the plurality of lead wires. The ceramic housing includes a plurality of insertion portions each including a through hole in which a corresponding one of the plurality of metal terminals is inserted, and at least one of the plurality of insertion portions has a different height from other insertion portions.

3 Claims, 10 Drawing Sheets

(56) References Cited

U.S. PATENT DOCUMENTS

| | | | |
|---|---|---|---|
| 2006/0288759 A1* | 12/2006 | Okumura | G01N 27/4062 73/31.05 |
| 2009/0071231 A1* | 3/2009 | Fujii | G01N 27/4077 73/31.05 |
| 2014/0260531 A1* | 9/2014 | Oba | G01N 27/4078 73/23.2 |
| 2018/0180570 A1 | 6/2018 | Hino | |

* cited by examiner

FIG. 8

[TABLE]

| | CONFIGURATION | h0 (mm) | h1 (mm) | h2 (mm) | Δh (mm) | EVALUATION |
|---|---|---|---|---|---|---|
| EXAMPLE 1 | FIG. 3 | 5.0 | 3.0 | — | 2.0 | A |
| EXAMPLE 2 | FIG. 3 | 5.0 | 1.0 | — | 4.0 | A |
| EXAMPLE 3 | FIG. 3 | 5.0 | 4.6 | — | 0.4 | A |
| EXAMPLE 4 | FIG. 3 | 8.0 | 0.2 | — | 7.8 | A |
| EXAMPLE 5 | FIG. 4A | 3.0 | 0.0 | — | 3.0 | A |
| EXAMPLE 6 | FIG. 4A | 9.0 | 0.0 | — | 9.0 | A |
| EXAMPLE 7 | FIG. 4A | 0.3 | 0.0 | — | 0.3 | A |
| EXAMPLE 8 | FIG. 4B | 3.0 | — | 2.0 | 5.0 | A |
| EXAMPLE 9 | FIG. 4B | 3.0 | — | 5.0 | 8.0 | A |
| EXAMPLE 10 | FIG. 4B | 3.0 | — | 0.2 | 3.2 | A |
| EXAMPLE 11 | FIG. 4B | 5.0 | — | 4.0 | 9.0 | A |
| COMPARATIVE EXAMPLE 1 | FIG. 3 (FIG. 5A) | 5.0 | 5.0 | — | 0.0 | B |
| COMPARATIVE EXAMPLE 2 | FIG. 3 (FIG. 5A) | 3.0 | 2.95 | — | 0.05 | B |
| COMPARATIVE EXAMPLE 3 | FIG. 4A (FIG. 5B) | 0.08 | 0.0 | — | 0.08 | B |
| COMPARATIVE EXAMPLE 4 | FIG. 4B (FIG. 5B) | 0.06 | — | 0.02 | 0.08 | B |

GAS SENSOR

CROSS-REFERENCE TO RELATED APPLICATION

This application is based upon and claims the benefit of priority from Japanese Patent Application No. 2019-204527 filed on Nov. 12, 2019, the contents of which are incorporated herein by reference.

BACKGROUND OF THE INVENTION

Field of the Invention

The present invention relates to a gas sensor for measuring the concentration of gas.

Description of the Related Art

The technique disclosed in Japanese Laid-Open Patent Publication No. 2018-105661 has an object to provide a gas sensor capable of preventing leakage current and maintaining high accuracy in detection of gas.

In order to achieve the object, in the gas sensor described in the patent publication, insertion-hole protrusions 42 of the same number as contact springs 3 protrude on an opposite end surface 401 of a spring insulator 4 that faces a plurality of connection terminals 51. The spring insulator 4 has a plurality of insertion holes 43 which open in end surfaces 424 of the insertion-hole protrusions 42 and an end surface 413 of support holes 41, and through which the plurality of contact springs 3 are inserted respectively.

SUMMARY OF THE INVENTION

In the gas sensor above, the metal terminals (contact springs 3) electrically connected to the sensor element are inserted through the insertion holes 43 of the insulator 4 and electrically connected to lead wires 52 in an elastic insulating member (bush 53).

Now, the metal terminals may vibrate when the gas sensor is subjected to vibration, for example. In this case, long-term or excessive application of vibrations, particularly those caused by bad road environments or by driving off road, for example, may cause the wall surfaces of the insertion holes 43 to be shaved and hence their inner diameters to be enlarged, which may cause the metal terminals to bend and short-circuit with each other.

The present invention has been made considering such a problem, and an object of the invention is to provide a gas sensor capable of reducing the possibility of short circuit between metal terminals.

A gas sensor according to an aspect of the invention includes a sensor element, an elastic insulating member, a plurality of lead wires, a plurality of metal terminals, and a ceramic housing. The plurality of lead wires are inserted in the elastic insulating member. The plurality of metal terminals each have a first end electrically connected to the sensor element, and a second end electrically connected to a corresponding one of the plurality of lead wires. The ceramic housing includes a plurality of insertion portions each including a through hole in which a corresponding one of the plurality of metal terminals is inserted, and at least one of the plurality of insertion portions has a different height from other of the insertion portions.

According to the present invention, it is possible to reduce the possibility of short circuit between the metal terminals.

The above and other objects, features, and advantages of the present invention will become more apparent from the following description when taken in conjunction with the accompanying drawings, in which a preferred embodiment of the present invention is shown by way of illustrative example.

BRIEF DESCRIPTION OF THE DRAWINGS

FIG. 8 is a table showing the results of testing with examples and comparative examples.

DESCRIPTION OF THE PREFERRED EMBODIMENTS

The gas sensor according to the present invention will be described below in detail in connection with preferred embodiments while referring to the accompanying drawings.

Figure 1:
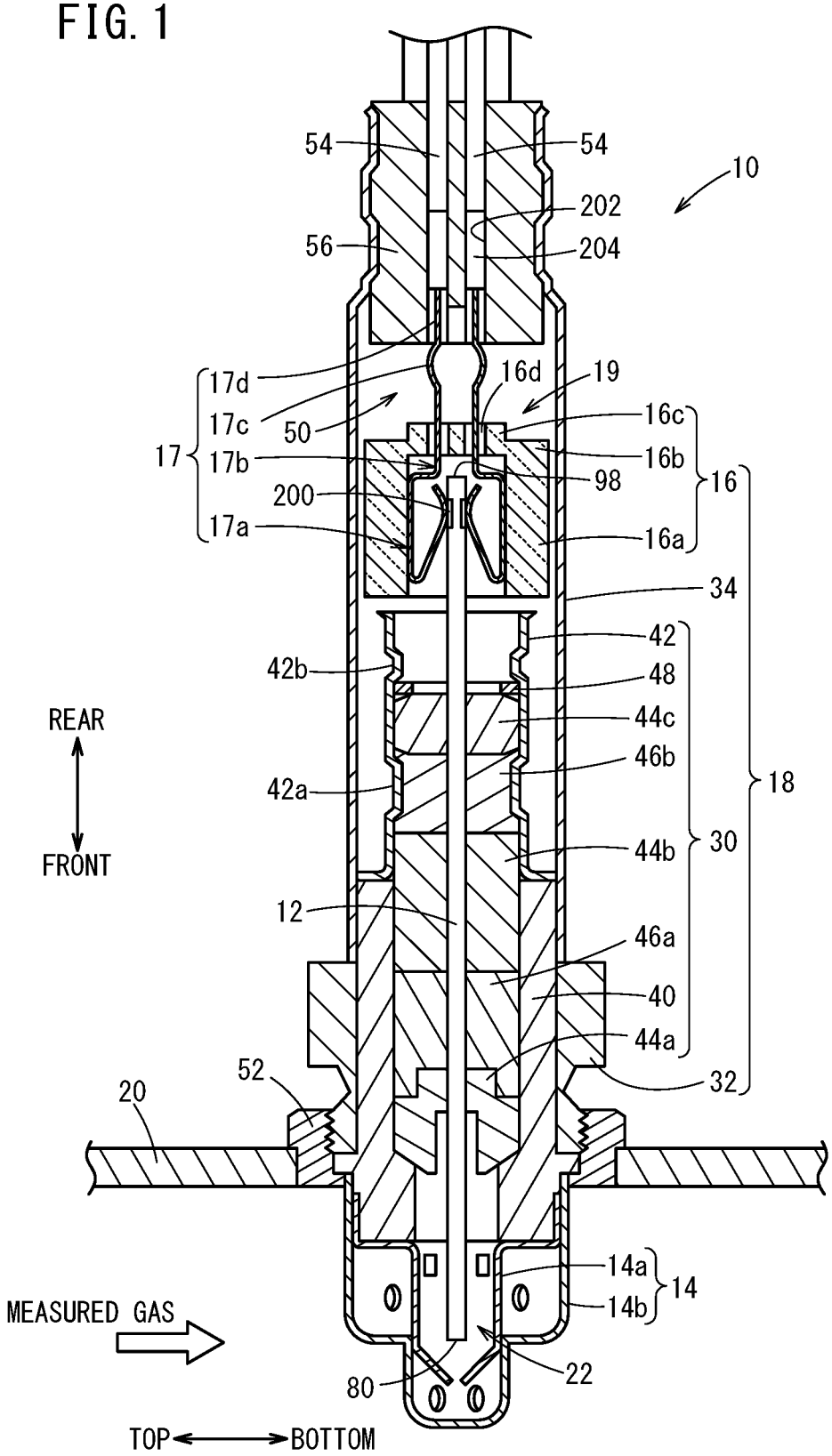
FIG. 1 is a cross section of a gas sensor according to an embodiment.

As shown in FIG. 1, a gas sensor 10 according to this embodiment includes a sensor element 12. The sensor element 12 has an elongated cuboidal shape. The longitudinal direction of the sensor element 12 (the left-right direction in FIG. 2) is defined as a front-rear direction, and the thickness direction of the sensor element 12 (the top-bottom direction in FIG. 2) is defined as a top-bottom direction. The width direction of the sensor element 12 (a direction vertical to the front-rear and top-bottom directions) is defined as a left-right direction.

As shown in FIG. 1, the gas sensor 10 includes the sensor element 12, a protective cover 14 for protecting the front end of the sensor element 12, and a sensor assembly 18 including a ceramic housing 16. The ceramic housing 16 holds a rear end portion of the sensor element 12, and functions as a connector 19 as metal terminals 17 electrically connected to the sensor element 12 are attached thereto.

As shown in the drawing, the gas sensor 10 is attached to a pipe 20 such as an exhaust gas pipe of a vehicle, for example, and used to measure concentrations of specific gases such as NOx, $O_2$, etc. that are contained in the exhaust gas as a gas to be measured (measured gas).

The protective cover 14 includes a bottomed-tube-like inner protective cover 14a covering the front end of the sensor element 12, and a bottomed-tube-like outer protective cover 14b covering the inner protective cover 14a. The inner protective cover 14a and the outer protective cover 14b have a plurality of holes through which the measured gas can flow into the interior of the protective cover 14. A sensor element cavity 22 is formed as a space enclosed by the inner protective cover 14a, and the front end of the sensor element 12 is disposed within the sensor element cavity 22.

The sensor assembly 18 includes an element seal body 30 for sealing and fixing the sensor element 12, a nut 32 attached to the element seal body 30, an outer tube 34, and the connector 19 that is in contact with and electrically connected to electrodes (not shown) that are formed on the surfaces (top and bottom surfaces) of the sensor element 12 in the rear part thereof.

The element seal body 30 includes a tubular main fitting 40, a tubular, inner tube 42 that is fixed by welding coaxially with the main fitting 40, and ceramic supporters 44a to 44c, powder compacts 46a, 46b, and a metal ring 48 which are sealed in a through hole in the interior of the main fitting 40 and the inner tube 42. The sensor element 12 is located on the center axis of the element seal body 30 and passes through the element seal body 30 in the front-rear direction. The inner tube 42 has a reduced-diameter portion 42a that presses the powder compact 46b toward the center axis of the inner tube 42, and a reduced-diameter portion 42b that presses frontward the ceramic supporters 44a to 44c and the powder compacts 46a, 46b through the metal ring 48. The pressing forces from the reduced-diameter portions 42a, 42b compress the powder compacts 46a, 46b between the main fitting 40 and inner tube 42 and the sensor element 12, whereby the powder compacts 46a, 46b provide a seal between the sensor element cavity 22 in the protective cover 14 and a space 50 in the outer tube 34 and fix the sensor element 12.

The nut 32 is fixed coaxially with the main fitting 40, and has a male thread portion on its outer periphery. The male thread portion of the nut 32 is inserted in a fixing member 52 that is welded to the pipe 20 and has a female thread on its inner periphery. The gas sensor 10 is thus fixed to the pipe 20 with the front end of the sensor element 12 and the protective cover 14 projecting in the pipe 20.

The outer tube 34 encloses the inner tube 42, the sensor element 12, and the connector 19, and a plurality of lead wires 54 connected to the metal terminals 17 of the connector 19 are drawn outside from the rear end of the outer tube 34. The lead wires 54 electrically conduct through the metal terminals 17 of the connector 19 to electrodes (described later) of the sensor element 12. The gap between the outer tube 34 and the lead wires 54 is sealed by an elastic insulating member 56 made of grommet or the like. The space 50 in the outer tube 34 is filled with a reference gas (the air in this embodiment). The rear end of the sensor element 12 is disposed within this space 50.

Figure 2:
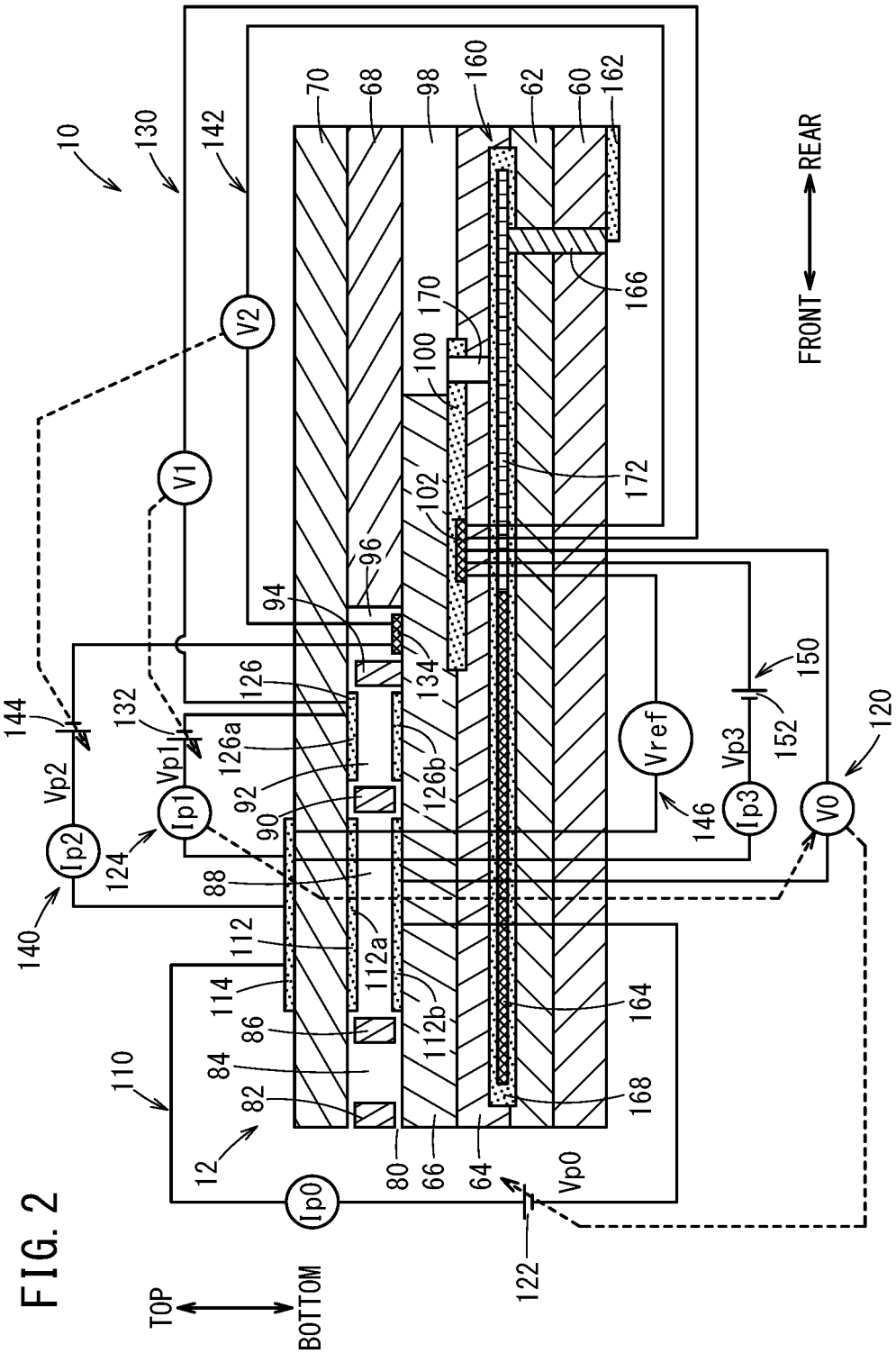
FIG. 2 is a schematic cross section schematically showing an exemplary configuration of a sensor element.

On the other hand, as shown in FIG. 2, the sensor element 12 is an element formed of a laminate in which six layers are laminated in this order from the bottom in the drawing, where the six layers include a first base layer 60, a second base layer 62, a third base layer 64, a first solid electrolyte layer 66, a spacer layer 68, and a second solid electrolyte layer 70, and the six layers are each formed of an oxygen ion conducting solid electrolyte layer, such as zirconia ($ZrO_2$), for example. In addition, the solid electrolyte forming the six layers is dense and gas-tight. The sensor element 12 is produced, for example, by applying given processing to, and printing circuit patterns on, ceramic green sheets corresponding to the individual layers, laminating these sheets together, and then integrating the sheets by sintering.

Between the lower surface of the second solid electrolyte layer 70 and the upper surface of the first solid electrolyte layer 66, on the side of one end of the sensor element 12 (on the left side in FIG. 2), a gas inlet 80, a first diffusion control portion 82, a buffer space 84, a second diffusion control portion 86, a first internal chamber 88, a third diffusion control portion 90, a second internal chamber 92, a fourth diffusion control portion 94, and a third internal chamber 96 are formed in such a manner that they are connected and adjoin in this order.

The gas inlet 80, the buffer space 84, the first internal chamber 88, the second internal chamber 92, and the third internal chamber 96 are formed by hollowing out the spacer layer 68, and are spaces in the sensor element 12 that are sectioned by the lower surface of the second solid electrolyte layer 70 at the top, the upper surface of the first solid electrolyte layer 66 at the bottom, and the side surfaces of the spacer layer 68 on the sides.

The first diffusion control portion 82, the second diffusion control portion 86, and the third diffusion control portion 90 are each formed as two oblong slits (the openings thereof have their longitudinal direction in the direction vertical to the drawing sheet). The fourth diffusion control portion 94 is formed as one oblong slit that is a gap under the lower surface of the second solid electrolyte layer 70 (the opening thereof has its longitudinal direction in the direction vertical to the drawing sheet). The section from the gas inlet 80 to the third internal chamber 96 will be referred to also as a measured gas passage.

A reference gas introduction space 98 is provided in a position farther from the above-mentioned one end than the measured gas passage. The reference gas introduction space 98 is formed between the upper surface of the third base layer 64 and the lower surface of the spacer layer 68 and is sectioned by a side surface of the first solid electrolyte layer 66 on the side. A reference gas for the measurement of NOx concentration, e.g., the air (the atmosphere within the space 50 in FIG. 1), is introduced into the reference gas introduction space 98.

An atmosphere introduction layer 100 is a layer made of ceramic such as porous alumina etc. and is exposed in the reference gas introduction space 98. Reference gas is introduced to the atmosphere introduction layer 100 through the reference gas introduction space 98. The atmosphere introduction layer 100 is formed so as to cover a reference electrode 102. The atmosphere introduction layer 100 introduces the reference gas in the reference gas introduction space 98 into the reference electrode 102 while providing given diffusion resistance to the reference gas. The atmosphere introduction layer 100 is formed in such a manner as to be exposed in the reference gas introduction space 98 only on the rear end side of the sensor element 12 on the right side of the reference electrode 102 (on the right side in FIG. 2). In other words, the reference gas introduction space 98 is not formed to a position right above the reference electrode 102. However, the reference electrode 102 may be formed right under the reference gas introduction space 98 in FIG. 2.

The reference electrode 102 is an electrode that is formed between the upper surface of the third base layer 64 and the first solid electrolyte layer 66, and, as mentioned above, the atmosphere introduction layer 100 connecting to the reference gas introduction space 98 is provided around the reference electrode 102. The reference electrode 102 is formed directly on the upper surface of the third base layer 64 and is covered by the atmosphere introduction layer 100 except in the part contacting the upper surface of the third base layer 64. Also, as will be described later, it is possible to measure the oxygen concentrations (oxygen partial pressures) in the first internal chamber 88, the second internal chamber 92, and the third internal chamber 96, by using the reference electrode 102. The reference electrode 102 is formed as a porous cermet electrode (e.g., a cermet electrode of Pt and $ZrO_2$).

In the measured gas passage, the gas inlet 80 is opened to the outside space, and the measured gas is taken into the sensor element 12 from the outside space through the gas inlet 80. The first diffusion control portion 82 is a portion that provides given diffusion resistance to the measured gas taken from the gas inlet 80. The buffer space 84 is a space that guides the measured gas introduced from the first diffusion control portion 82 to the second diffusion control portion 86. The second diffusion control portion 86 is a portion that provides given diffusion resistance to the measured gas introduced from the buffer space 84 into the first internal chamber 88. When the measured gas is introduced from the outside of the sensor element 12 into the first internal chamber 88, the measured gas rapidly taken into the sensor element 12 from the gas inlet 80 due to pressure fluctuation of the measured gas in the outside space (the pressure fluctuation can be exhaust pressure pulsation if the measured gas is an automotive exhaust gas) is not directly introduced into the first internal chamber 88 but is introduced into the first internal chamber 88 after concentration variation of the measured gas is cancelled through the first diffusion control portion 82, the buffer space 84, and the second diffusion control portion 86. Accordingly, the concentration variation of the measured gas introduced into the first internal chamber 88 has become almost negligible. The first internal chamber 88 is provided as a space that adjusts the oxygen partial pressure in the measured gas introduced through the second diffusion control portion 86. The oxygen partial pressure is adjusted by operation of a main pump cell 110 described next.

The main pump cell 110 is an electrochemical pump cell formed of an inside pumping electrode 112 provided on the internal surfaces of the first internal chamber 88, an outside pumping electrode 114 formed on the upper surface of the second solid electrolyte layer 70 in such a manner as to be exposed to the outside space (the sensor element cavity 22 in FIG. 1) in an area corresponding to the inside pumping electrode 112, and the second solid electrolyte layer 70 sandwiched between the inside pumping electrode 112 and the outside pumping electrode 114.

The inside pumping electrode 112 is formed on the upper and lower solid electrolyte layers (the second solid electrolyte layer 70 and the first solid electrolyte layer 66) that section the first internal chamber 88, and on the spacer layer 68 that forms the side walls of the first internal chamber 88. Specifically, a ceiling electrode portion 112*a* of the inside pumping electrode 112 is formed on the lower surface of the second solid electrolyte layer 70 forming the ceiling surface of the first internal chamber 88, a bottom electrode portion 112*b* is formed directly on the upper surface of the first solid electrolyte layer 66 forming the bottom surface of the first internal chamber 88, and side electrode portions (not shown) connecting the ceiling electrode portion 112*a* and the bottom electrode portion 112*b* are formed on the side wall surfaces (internal surfaces) of the spacer layer 68 forming both side walls of the first internal chamber 88. That is, the inside pumping electrode 112 is formed as a structure like a tunnel in the part where the side electrode portions are disposed.

The inside pumping electrode 112 and the outside pumping electrode 114 are formed as porous cermet electrodes (e.g., cermet electrodes of Pt and $ZrO_2$ containing 1% Au). The inside pumping electrode 112 that contacts the measured gas is formed using a material having a weakened reduction ability for NOx components in the measured gas.

In the main pump cell 110, a desired pumping voltage Vp0 is applied across the inside pumping electrode 112 and the outside pumping electrode 114 to cause a pumping current Ip0 to flow in the positive direction or negative direction between the inside pumping electrode 112 and the outside pumping electrode 114, which enables the main pump cell 110 to pump out the oxygen in the first internal chamber 88 to the outside space, or to pump the oxygen in the outside space into the first internal chamber 88.

Further, in order to detect the oxygen concentration (oxygen partial pressure) in the atmosphere in the first internal chamber 88, a main-pump-controlling oxygen-partial-pressure-detecting sensor cell 120, which is an electrochemical sensor cell, is formed of the inside pumping electrode 112, the second solid electrolyte layer 70, the spacer layer 68, the first solid electrolyte layer 66, and the reference electrode 102.

The oxygen concentration (oxygen partial pressure) in the first internal chamber 88 is known by measuring an electromotive force V0 in the main-pump-controlling oxygen-partial-pressure-detecting sensor cell 120. Further, the pumping current Ip0 is controlled by feedback-controlling the pumping voltage Vp0 of a variable power supply 122 so as to keep the electromotive force V0 constant. The oxygen concentration in the first internal chamber 88 can thus be maintained at a certain constant value.

The third diffusion control portion 90 is a portion that provides given diffusion resistance to the measured gas whose oxygen concentration (oxygen partial pressure) has been controlled by the operation of the main pump cell 110 in the first internal chamber 88, and the third diffusion control portion 90 guides the measured gas into the second internal chamber 92.

The second internal chamber 92 is provided as a space in which the measured gas, which has undergone oxygen concentration (oxygen partial pressure) adjustment in the first internal chamber 88 in advance and then introduced through the third diffusion control portion 90, is subjected to further oxygen partial pressure adjustment by an auxiliary pump cell 124. The oxygen concentration in the second internal chamber 92 can thus be kept constant highly accurately, enabling the gas sensor 10 to perform highly accurate NOx concentration measurement.

The auxiliary pump cell 124 is an auxiliary electrochemical pump cell including an auxiliary pumping electrode 126 provided on the inner surfaces of the second internal chamber 92, the outside pumping electrode 114, and the second solid electrolyte layer 70, where the outside pumping electrode 114 can be another appropriate electrode outside of the sensor element 12.

The auxiliary pumping electrode 126 has a tunnel-like structure similar to that of the inside pumping electrode 112 provided in the first internal chamber 88, and is disposed in the second internal chamber 92. That is, a ceiling electrode portion 126*a* is formed on the second solid electrolyte layer 70 forming the ceiling surface of the second internal chamber 92, a bottom electrode portion 126*b* is formed directly on the upper surface of the first solid electrolyte layer 66 forming the bottom surface of the second internal chamber 92, and side electrode portions (not shown) connecting the ceiling electrode portion 126*a* and the bottom electrode portion 126*b* are formed on both wall surfaces of the spacer layer 68 forming the side walls of the second internal chamber 92, thus forming a tunnel-like structure. Similarly to the inside pumping electrode 112, the auxiliary pumping electrode 126 is also formed using a material having a weakened reduction ability for NOx components in the measured gas.

In the auxiliary pump cell 124, a desired voltage Vp1 is applied across the auxiliary pumping electrode 126 and the outside pumping electrode 114, whereby the auxiliary pump cell 124 can pump out the oxygen in the atmosphere in the second internal chamber 92 to the outside space, or to pump oxygen into the second internal chamber 92 from the outside space.

Further, in order to control the oxygen partial pressure in the atmosphere in the second internal chamber 92, an auxiliary-pump-controlling oxygen-partial-pressure-detecting sensor cell 130, which is an electrochemical sensor cell, is formed of the auxiliary pumping electrode 126, the reference electrode 102, the second solid electrolyte layer 70, the spacer layer 68, and the first solid electrolyte layer 66.

The auxiliary pump cell 124 performs pumping with a variable power supply 132 that is voltage-controlled based on an electromotive force V1 detected by the auxiliary-pump-controlling oxygen-partial-pressure-detecting sensor cell 130. Thus, the oxygen partial pressure in the atmosphere in the second internal chamber 92 can be controlled to such low partial pressure as not to substantially affect the measurement of NOx.

In addition, a pumping current Ip1 thereof is used to control the electromotive force V0 of the main-pump-controlling oxygen-partial-pressure-detecting sensor cell 120. Specifically, the pumping current Ip1 is input as a control signal to the main-pump-controlling oxygen-partial-pressure-detecting sensor cell 120 to thereby control the electromotive force V0, whereby a control is provided so that the gradient of oxygen partial pressure in the measured gas introduced from the third diffusion control portion 90 into the second internal chamber 92 can always be kept constant. When the gas sensor is used as a NOx sensor, the main pump cell 110 and the auxiliary pump cell 124 operate to keep the oxygen concentration in the second internal chamber 92 at a constant value of about 0.001 ppm.

The fourth diffusion control portion 94 is a portion that provides given diffusion resistance to the measured gas whose oxygen concentration (oxygen partial pressure) has been controlled by the operation of the auxiliary pump cell 124 in the second internal chamber 92, and the fourth diffusion control portion 94 guides the measured gas into the third internal chamber 96. The fourth diffusion control portion 94 serves to limit the amount of NOx flowing into the third internal chamber 96.

The third internal chamber 96 is provided as a space for performing processing to measure nitrogen oxide (NOx) concentration in the measured gas, which has undergone oxygen concentration (oxygen partial pressure) adjustment in the second internal chamber 92 in advance and then introduced through the fourth diffusion control portion 94. The measurement of NOx concentration is mainly performed in the third internal chamber 96 by operation of a measurement pump cell 140.

The measurement pump cell 140 measures the NOx concentration in the measured gas in the third internal chamber 96. The measurement pump cell 140 is an electrochemical pump cell formed of a measurement electrode 134 formed directly on the upper surface of the first solid electrolyte layer 66 facing the third internal chamber 96, the outside pumping electrode 114, the second solid electrolyte layer 70, the spacer layer 68, and the first solid electrolyte layer 66. The measurement electrode 134 is a porous cermet electrode. The measurement electrode 134 functions also as a NOx reduction catalyst that reduces the NOx present in the atmosphere in the third internal chamber 96.

In the measurement pump cell 140, the oxygen generated by the decomposition of nitrogen oxide in the atmosphere around the measurement electrode 134 is pumped out, and the amount thereof can be detected as a pumping current Ip2.

Further, in order to detect the oxygen partial pressure around the measurement electrode 134, an electrochemical sensor cell, i.e., a measurement-pump-controlling oxygen-partial-pressure-detecting sensor cell 142, is formed of the first solid electrolyte layer 66, the measurement electrode 134, and the reference electrode 102. A variable power supply 144 is controlled based on an electromotive force V2 detected by the measurement-pump-controlling oxygen-partial-pressure-detecting sensor cell 142.

The measured gas guided into the second internal chamber 92 reaches the measurement electrode 134 in the third internal chamber 96 through the fourth diffusion control portion 94 in a state where oxygen partial pressure is controlled. The nitrogen oxide in the measured gas around the measurement electrode 134 is reduced to generate oxygen ($2NO \rightarrow N_2 + O_2$). Then, the oxygen thus generated is pumped by the measurement pump cell 140. In this process, a voltage Vp2 of the variable power supply 144 is controlled so that the electromotive force V2 detected by the measurement-pump-controlling oxygen-partial-pressure-detecting sensor cell 142 is kept constant. The amount of oxygen generated around the measurement electrode 134 is proportional to the concentration of the nitrogen oxide in the measured gas, and therefore the nitrogen oxide concentration in the measured gas is calculated using the pumping current Ip2 of the measurement pump cell 140.

Further, an electrochemical sensor cell 146 is formed of the second solid electrolyte layer 70, the spacer layer 68, the first solid electrolyte layer 66, the third base layer 64, the outside pumping electrode 114, and the reference electrode 102, and the oxygen partial pressure in the measured gas outside of the sensor can be detected by an electromotive force Vref obtained by the sensor cell 146.

Further, an electrochemical reference-gas-adjustment pump cell 150 is formed of the second solid electrolyte layer 70, the spacer layer 68, the first solid electrolyte layer 66, the third base layer 64, the outside pumping electrode 114, and the reference electrode 102. The reference-gas-adjustment pump cell 150 performs pumping as a voltage Vp3 applied by a variable power supply 152 connected between the outside pumping electrode 114 and the reference electrode 102 causes a control current Ip3 to flow. The reference-gas-adjustment pump cell 150 thus pumps oxygen into the space (atmosphere introduction layer 100) around the reference electrode 102 from the space (the sensor element cavity 22 in FIG. 1) around the outside pumping electrode 114. The voltage Vp3 of the variable power supply 152 is determined in advance as a direct-current voltage such that the control current Ip3 becomes a given value (a dc current with a constant value).

In the gas sensor 10 constructed as described above, the main pump cell 110 and the auxiliary pump cell 124 are operated so that the measurement pump cell 140 is supplied with the measured gas in which the oxygen partial pressure is always kept at a constant low value (a value that does not substantially affect the NOx measurement). Thus, the NOx concentration in the measured gas can be known based on the pumping current Ip2 that flows in substantially proportion to the NOx concentration in the measured gas as the oxygen generated by NOx reduction is pumped out by the measurement pump cell 140.

In order to enhance the oxygen ion conductivity of the solid electrolyte, the sensor element 12 further includes a heater unit 160 that serves as a temperature controller which heats the sensor element 12 and keeps the temperature. The heater unit 160 includes a heater connector electrode 162, a heater 164, a through hole 166, a heater insulating layer 168, a pressure diffusion hole 170, and a lead wire 172.

The heater connector electrode 162 is an electrode that is formed in contact with the lower surface of the first base layer 60. The heater connector electrode 162 is connected to an external power supply to supply electricity to the heater unit 160 from outside.

The heater 164 is an electric resistor that is sandwiched from above and below between the second base layer 62 and the third base layer 64. The heater 164 is connected to the heater connector electrode 162 through the lead wire 172 and the through hole 166, where the heater 164 generates heat by being supplied with electricity from outside through the heater connector electrode 162, thereby heating the solid electrolyte forming the sensor element 12 and keeping the temperature.

Further, the heater 164 is buried in the entire area from the first internal chamber 88 to the third internal chamber 96, so that the entire sensor element 12 can be adjusted to temperatures at which the solid electrolyte is activated.

The heater insulating layer 168 is an insulating layer formed on the upper and lower surfaces of the heater 164, and made of porous alumina formed of an insulator of alumina etc. The heater insulating layer 168 is formed for the purpose of obtaining electric insulation between the second base layer 62 and the heater 164 and electric insulation between the third base layer 64 and the heater 164.

The pressure diffusion hole 170 passes through the third base layer 64 to communicate with the reference gas introduction space 98, in order to reduce internal pressure increase caused by temperature rise in the heater insulating layer 168.

The variable power supplies 122, 144, 132, 152, etc. shown in FIG. 2 are connected to electrodes through lead wires (not shown) actually formed in the sensor element 12 and the connector 19 and lead wires 54 in FIG. 1.

Now, in this embodiment, the metal terminals 17 extending rearward are electrically connected to corresponding connection terminals 200 that are exposed from the rear end portion of the sensor element 12. The ceramic housing 16 is provided around the rear end portion of the sensor element 12, and the metal terminals 17 are fitted between the connection terminals 200 and the ceramic housing 16, whereby the connection terminals 200 of the sensor element 12 and the metal terminals 17 are press fitted and electrically connected together. That is, the ceramic housing 16 is attached with the metal terminals 17 electrically connected to the sensor element 12 and holds the rear end portion of the sensor element 12.

The rear ends of the metal terminals 17 extend rearward behind the ceramic housing 16 and are electrically connected to the lead wires 54 inserted in the elastic insulating member 56. The elastic insulating member 56 has a plurality of through holes 202 along the axial direction of the sensor element 12. The lead wires 54 are inserted through the through holes 202, and the metal terminals 17 extending from the sensor element 12 and the lead wires 54 are electrically connected by solder 204.

More specifically, each metal terminal 17 can be divided into a sensor-connected portion 17a, a through hole passing portion 17b, a bending portion 17c, and a lead wire-connected portion 17d. The sensor-connected portion 17a has a substantially linear portion and an arc-shaped portion, and functions as a contact spring. The arc-shaped portion comes in elastic contact with the connection terminal 200 of the sensor element 12. The through hole passing portion 17b passes through (is inserted in) a through hole 16d (described later) of the ceramic housing 16. The bending portion 17c has a bending in the form of substantially an arc, and presents flexibility so that excessive stress will not act on the metal terminal 17 when the metal terminal 17 connects the connection terminal 200 (sensor element 12) and the lead wire 54. The lead wire-connected portion 17d is electrically connected to the lead wire 54 (solder 204).

Figure 3:
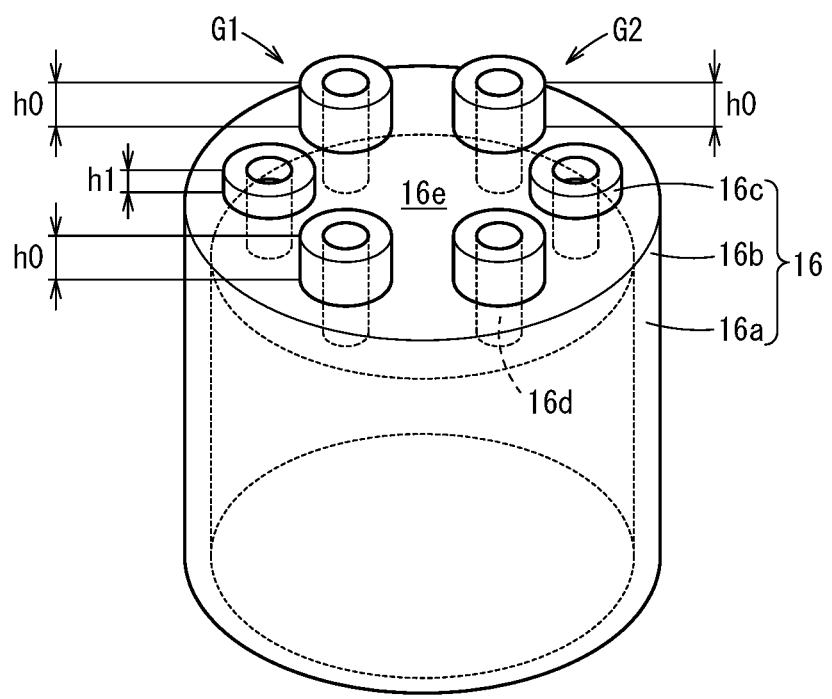
FIG. 3 is a schematic perspective view illustrating a ceramic housing of the embodiment.

A description will be given referring to FIGS. 1 and 3. FIG. 3 is a perspective view illustrating the ceramic housing 16 of the embodiment in an enlarged manner. The ceramic housing 16 is made of ceramic and includes a tubular portion 16a, a disk portion 16b, insertion portions 16c, and through holes 16d. The tubular portion 16a has a substantially cylindrical shape and holds, within its inner space, the rear portion of the sensor element 12, the connection terminals 200, and the sensor-connected portions 17a of the metal terminals 17. The disk portion 16b has a substantially disk-like shape, and the insertion portions 16c are arranged on its end surface 16e (the rear end surface of the ceramic housing 16). The end surface 16e can be substantially a flat surface. The insertion portions 16c are portions through which the metal terminals 17 are inserted. The insertion portions 16c each have the through hole 16d into which the metal terminal 17 is inserted. The through holes 16d pass through the disk portion 16b and the respective insertion portions 16c, and the metal terminals 17, particularly the through hole passing portions 17b thereof, are inserted into the through holes 16d, respectively.

In this example, six insertion portions 16c are arranged in correspondence with six metal terminals 17, each insertion portion 16c having a single through hole 16d. More specifically, groups G1 and G2, each including three insertion portions 16c, are arranged along the circumference of the disk portion 16b. The insertion portions 16c in each group G1, G2 are arranged at substantially equal intervals along the circumference of the disk portion 16b. The intervals between the groups G1 and G2 (e.g., the interval between the insertion portion 16c at the end of the group G1 and the insertion portion 16c at the end of the group G2 that is closest to this insertion portion 16c of the group G1) are larger than the intervals between the insertion portions 16c within each group G1, G2.

Each insertion portion 16c protrudes (has a height) from the top surface of the disk portion 16b and functions as a base. The heights of the insertion portions 16c are not all equal. For example, a height h1 of the center insertion portion 16c in each group G1, G2 differs from a height h0 of the insertion portions 16c on both sides thereof (at both ends). As will be explained later, the configuration in which the heights of all the insertion portions 16c are not equal reduces damage to (bending of) the metal terminals 17, particularly damage to the through hole passing portions 17b thereof.

In this embodiment, insertion portions 16c having different heights are positioned adjacent to each other in each of the groups G1, G2. This configuration reduces the damage further effectively. As will be explained later, it is thought that the presence of the adjacent insertion portion 16c affects the damage.

On the other hand, between the groups G1 and G2, insertion portions 16c with different heights are not located adjacent to each other (the insertion portion 16c at the end of the group G1 has the same height h0 as the insertion portion 16c at the end of the group G2 that is closest thereto). That is, it is not necessary that the insertion portions 16c with different heights be located adjacent to each other between the groups G1 and G2. The intervals between the insertion portions 16c of the group G1, and the insertion portions 16c of the group G2, are larger than the intervals between the insertion portions 16c within each group G1, G2. It is therefore thought that the presence of the insertion portions 16c between the groups G1 and G2 only slightly affects the damage to the through hole passing portions 17b.

A difference $\Delta h$ (=|h1−h0|) between the heights of the insertion portions 16c is from 0.3 to 10.0 mm, for example. The damage to the through hole passing portions 17b can be reduced when the height difference $\Delta h$ is in this range. It is assumed here that the height h1 is smaller than the height h0, but the height h1 may be larger than the height h0.

In this example, the plurality of insertion portions 16c (the bases here) are spaced apart from each other on the top surface of the disk portion 16b, but in a modification, the plurality of insertion portions 16c may be connected to each other. In this case, the insertion portions 16c with different heights may be connected together. That is, the insertion portion 16c may have parts with different heights, and the through hole 16d may be formed in each of the parts.

Further, the number of the groups of the insertion portions 16c, and the number of the insertion portions 16c in each group, can be set suitably. For example, one group may include two, or four or more insertion portions 16c. Also, the number of groups may be three, four or more, or one.

Figure 4A:
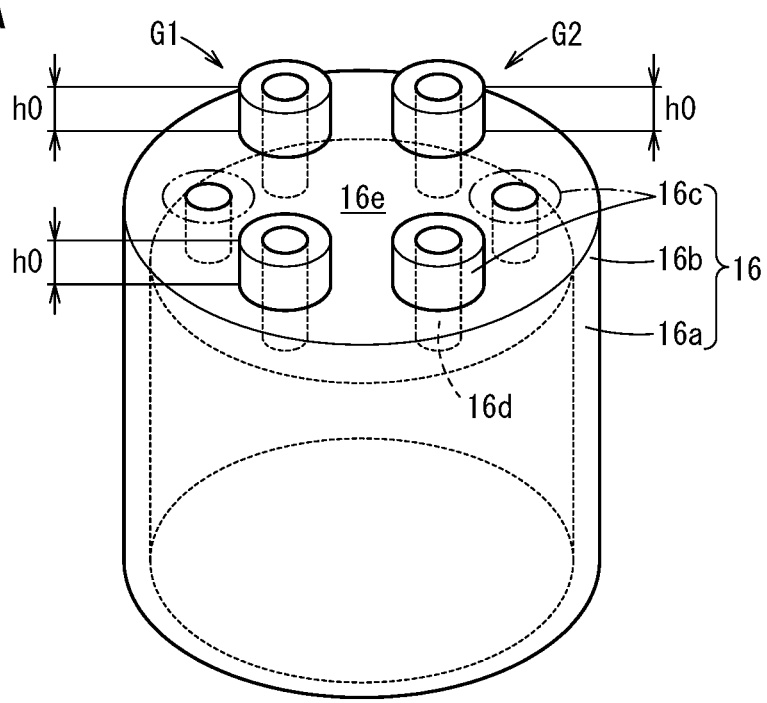
FIGS. 4A, 4B, and 4C are perspective views illustrating ceramic housings of modifications.
Figure 4B:
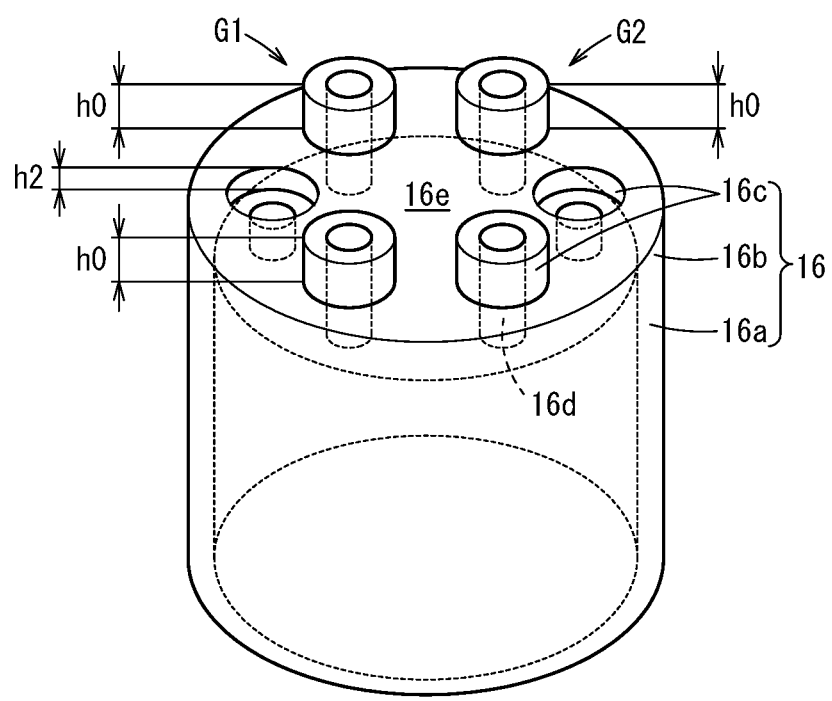
Figure 4C:
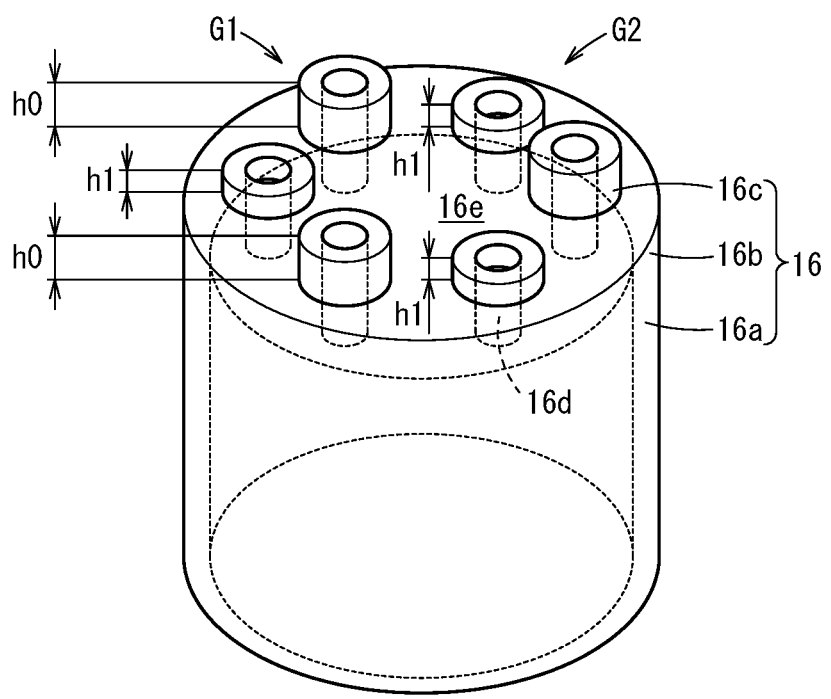

FIGS. 4A to 4C are perspective views showing modifications of the insertion portions 16c. FIG. 4A shows a configuration in which the end surface of the central insertion portion 16c in each group G1, G2 is arranged to be flush with the top surface of the disk portion 16b (the height h1 of these insertion portions 16c=0). In this case, the height difference $\Delta h$ is h0. FIG. 4B shows a configuration in which the end surface of the central insertion portion 16c in each group G1, G2 is lower (recessed) by a height h2 than the top surface of the disk portion 16b. In this case, the height difference $\Delta h$ is h0+h2. In this way, the end surfaces of the insertion portions 16c need not necessarily protrude from the top surface of the disk portion 16b. In FIG. 4C, the insertion portions 16c having the heights h0, h1 are arranged alternately not only within each group G1, G2 but also in the entirety of the groups G1 and G2. In any of these examples, the height difference $\Delta h$ is from 0.3 to 10.0 mm, for example.

Figure 5A:
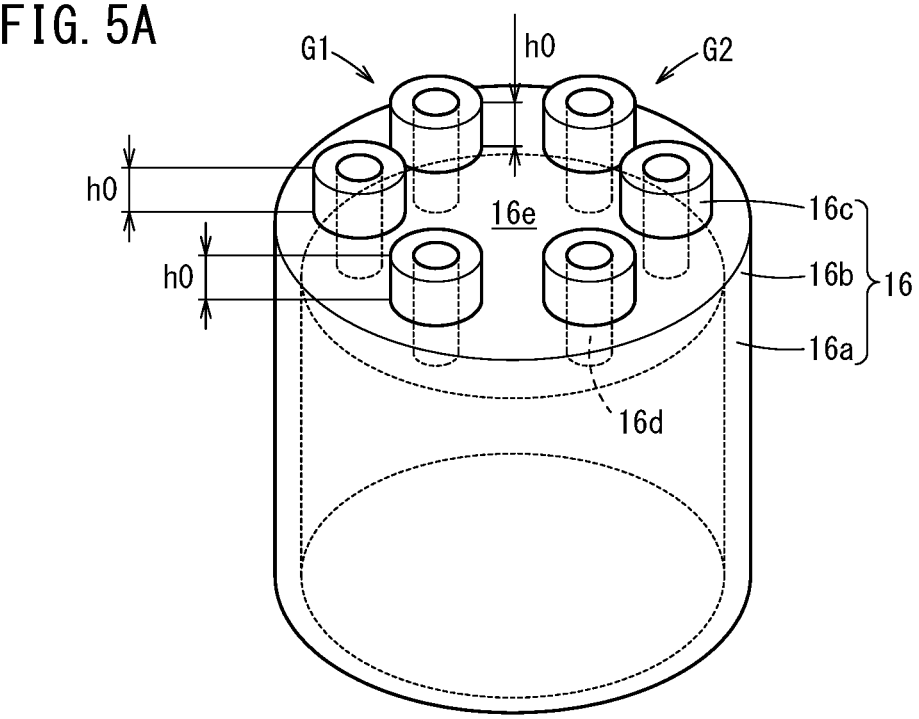
FIGS. 5A and 5B are perspective views illustrating ceramic housings of comparative examples.
Figure 5B:
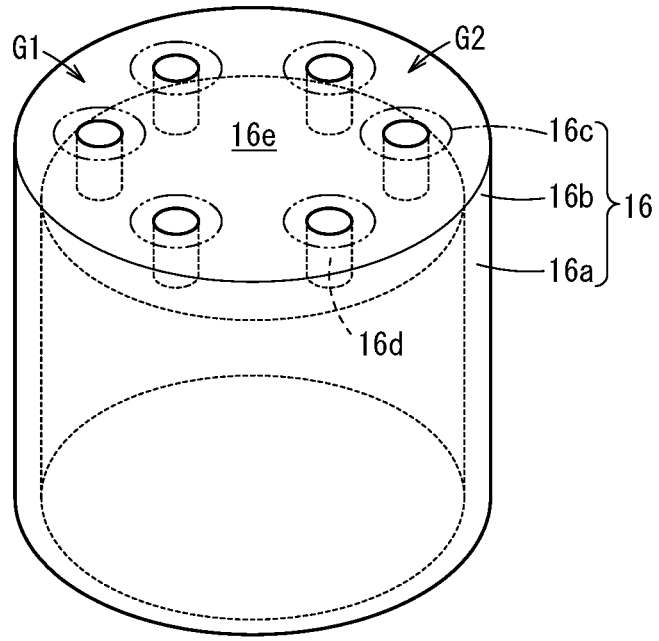

FIGS. 5A and 5B are perspective views illustrating comparative examples of the insertion portions 16c. In FIG. 5A, the heights h0 of all the insertion portions 16c are equal. In FIG. 5B, the end surfaces of all the insertion portions 16c are flush with the top surface of the disk portion 16b.

EXAMPLES

Now, an example experiment for checking damage to the metal terminals 17 caused by an application of vibration with examples and comparative examples will be described.

Testing and evaluations were conducted with examples 1 to 11 and comparative examples 1 to 4. The examples and comparative examples included the ceramic housings 16 constructed as shown in FIG. 3, 4A, or 4B, with six metal terminals 17. Specifically, the examples 1 to 4 and comparative examples 1 and 2 had the structure of FIG. 3, the examples 5 to 7 and comparative example 3 had the structure of FIG. 4A, and the examples 8 to 11 and comparative example 4 had the structure of FIG. 4B. In fact, the comparative examples 1 and 2 substantially had the structure of FIG. 5A, and the comparative examples 3 and 4 substantially had the structure of FIG. 5B, but, for convenience, the drawings of the embodiment were used to show the heights h1 and h2.

In the examples 1 to 11 and the comparative examples 1 to 4, the height h0 was 5.0, 5.0, 5.0, 8.0, 3.0, 9.0, 0.3, 3.0, 3.0, 3.0, 5.0, 5.0, 3.0, 0.08, and 0.06 [mm], respectively.

The height h1 in the examples 1 to 7 was 3.0, 1.0, 4.6, 0.2, 0.0, 0.0 and 0.0, and the height h1 in the comparative examples 1 to 3 was 5.0, 2.95, and 0.0 [mm], respectively. The height h2 in the examples 8 to 11 and the comparative example 4 was 2.0, 5.0, 0.2, 4.0, and 0.02 [mm], respectively.

As a result, in the examples 1 to 11 and the comparative examples 1 to 4, the height difference $\Delta h$ (=h0−h1, or h0+h2) was 2.0, 4.0, 0.4, 7.8, 3.0, 9.0, 0.3, 5.0, 8.0, 3.2, 9.0, 0.0, 0.05, 0.08, and 0.08 [mm], respectively.

[Evaluation Method]

The states of electrical connection of the metal terminals 17 after subjected to vibration testing were evaluated. Specifically, measurements were conducted to check the conditions (1) and (2) below.

(1) Whether a short circuit is present between the metal terminals 17 after testing.

(2) A ratio R (=D1/D0) of intervals between the through holes 16d between before and after testing.

Where D0: the interval between the through holes 16d before testing, and D1: the interval between the through holes 16d after testing.

As will be explained later, the inner walls of the through holes 16d of the ceramic housing 16 are worn by the vibration, and then the diameters of the inner walls enlarge, which may cause the metal terminals 17 to come closer and get short-circuited. For this reason, the evaluations were made not only to check whether the metal terminals 17 were short-circuited but also to check the enlargement of the diameters of the through holes 16d (the shortening of the interval between adjacent through holes 16d) that precedes the short circuiting.

Criteria for the evaluation were set as follows.

A: (1) No short circuit is present between the metal terminals 17, and (2) the ratio R is larger than 1/10.

B: (1) The metal terminals 17 are short-circuited, or (2) the ratio R is equal to or less than 1/10.

[Experiment Method]

Gas sensors were attached to a chamber and tested under the following vibration conditions.

Frequency: 250 Hz
Acceleration: 50 G
Test time: 500 hours
Gas temperature: room temperature As the results of testing, as shown in Table of FIG. 8, the evaluations of the examples 1 to 11 were A, but the evaluations of the comparative examples 1 to 4 were B. That is, the evaluations differed between samples with larger height differences $\Delta h$ ($\Delta h$ of 0.3 or more) and samples with smaller height differences $\Delta h$ ($\Delta h$ of 0.08 or less).

Figure 6A:
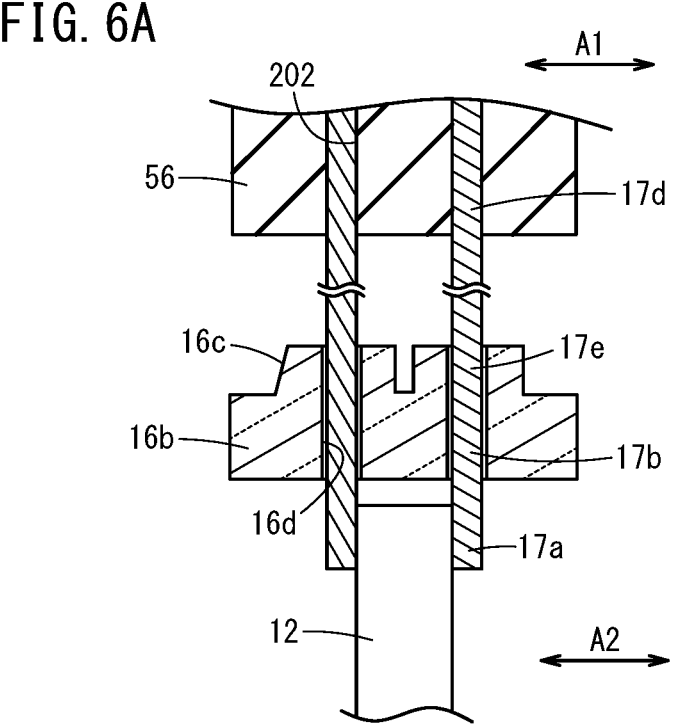
FIGS. 6A and 6B are schematic cross sections illustrating conditions before and after an application of vibration with a comparative example.
Figure 6B:
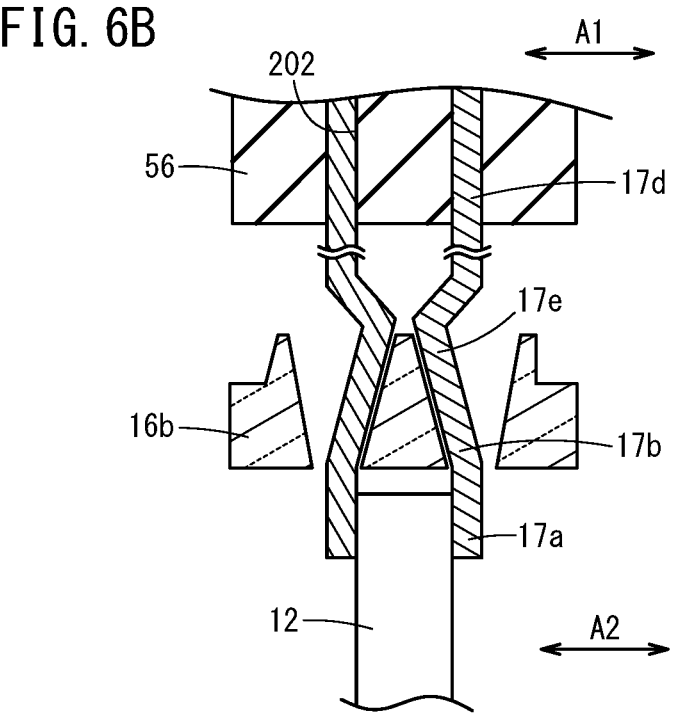
Figure 7A:
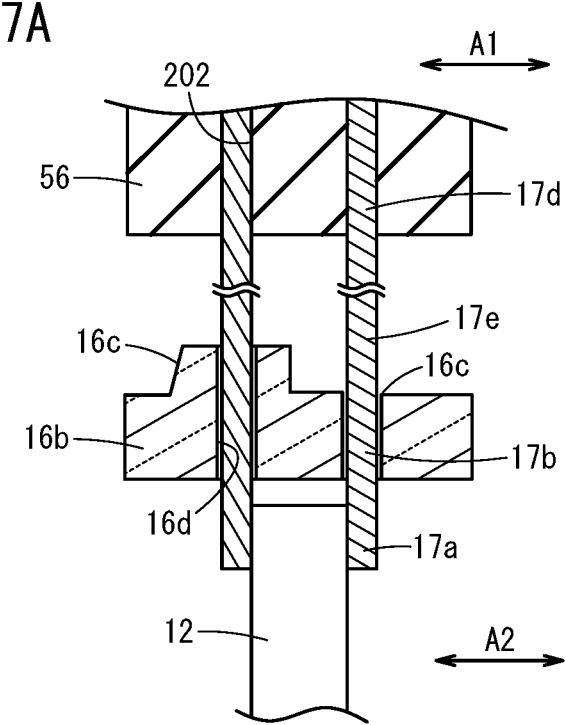
FIGS. 7A and 7B are schematic cross sections illustrating conditions before and after an application of vibration with an example 1.
Figure 7B:
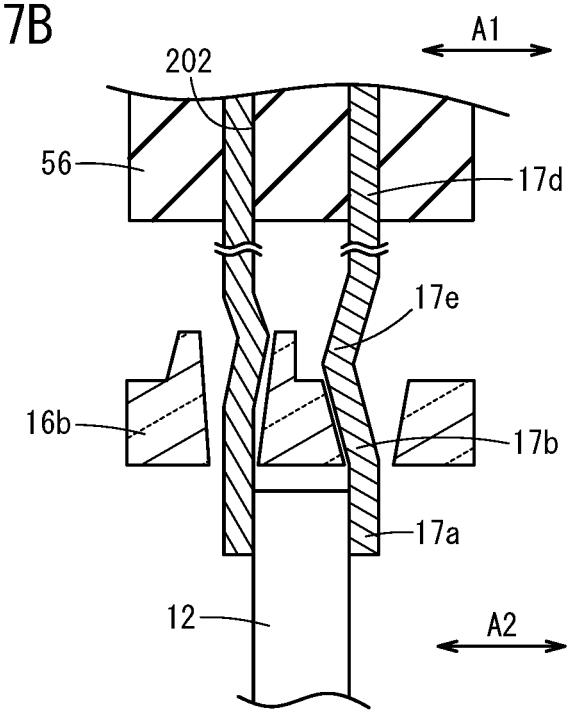

FIGS. 6A to 7B are schematic cross sections illustrating how the examples and comparative examples yielded different results in the comparative experiment. FIGS. 6A and 6B are schematic cross sections illustrating conditions in the vicinity of the ceramic housing 16 of a comparative example before and after the application of vibration, respectively. FIGS. 7A and 7B are schematic cross sections illustrating conditions in the vicinity of the ceramic housing 16 of the example 1 before and after the application of vibration, respectively. As shown in FIGS. 6A and 7A, the comparative example and the example 1 differ in that the heights of adjacent insertion portions 16c are equal in the comparative example, whereas the heights are different in the example 1.

When vibration is applied to the gas sensor, an amplitude A1 of the vibration applied to the elastic insulating member 56 is relatively large, but an amplitude A2 of the vibration applied to the ceramic housing 16 is relatively small. The gas sensor vibrates with the ceramic housing 16 as a fixed end and the elastic insulating member 56 as a free end, and therefore the amplitude on the elastic insulating member 56 side (free end side) is larger.

Due to the difference in amplitude, the inner walls of the insertion portions 16c of the ceramic housing 16 and the through holes 16d of the disk portion 16b are worn more significantly on the side closer to the elastic insulating member 56, and therefore the diameters thereof enlarge to a greater extent. As a result, the through holes 16d are tapered into a shape of an upside-down truncated cone (see FIGS. 6B and 7B).

At this time, as shown in FIG. 6B, in the comparative example, both insertion portions 16c are worn relatively uniformly. In contrast, as shown in FIG. 7B, in the example 1, the wear of the taller insertion portion 16c is restricted due to the height difference between the insertion portions 16c. As a result, the through hole passing portions 17b of the comparative example bend and are likely to short-circuit on the elastic insulating member 56 side, but the bending of the through hole passing portions 17b in the example 1 is restricted and they are less likely to short-circuit on the elastic insulating member 56 side.

The difference in the wear of the inner walls of the through holes 16d due to the heights can be explained as follows. As shown in FIGS. 6A and 6B, in the comparative example, rear parts 17e of the through hole passing portions 17b of adjacent metal terminals 17 are both in contact with the ceramic housing 16 (with the insertion portions 16c). It is therefore thought that the vibrations of the rear parts 17e of the adjacent through hole passing portions 17b interact to contribute to the wear of the insertion portions 16c. In contrast, in the example 1, the rear part 17e in the shorter insertion portion 16c is not in contact with the ceramic housing 16. It is therefore thought that the vibration of the rear part 17e in the shorter insertion portion 16c does not contribute to the wear of the taller insertion portion 16c. In this way, adjacent metal terminals 17 contact the ceramic housing 16 (insertion portions 16c) in different manners in the presence of a height difference between the through holes 16d. It is thought that this fact produced the difference in the conditions of wear of the ceramic housing 16, especially on the side closer to the elastic insulating member 56.

Invention Obtained from Embodiments

The invention obtained from the embodiments described above will be recited below.

[1] A gas sensor 10 of the embodiment includes a sensor element 12, an elastic insulating member 56, a plurality of lead wires 54, a plurality of metal terminals 17, and a ceramic housing 16. The plurality of lead wires 54 are inserted in the elastic insulating member 56. The plurality of metal terminals 17 each have a first end (sensor-connected portion 17a) electrically connected to the sensor element 12, and a second end (lead wire-connected portion 17d) electrically connected to a corresponding one of the plurality of lead wires 54. The ceramic housing 16 includes a plurality of insertion portions 16c each including a through hole 16d in which a corresponding one of the plurality of metal terminals 17 is inserted, and at least one of the plurality of insertion portions 16c has a different height from other insertion portions 16c.

This configuration reduces wear of the insertion portions 16c (through holes 16d) when the gas sensor 10 is subjected to vibration, and thereby reduces the possibility of short circuit that would occur if the metal terminals 17 bend and contact each other.

[2] In the embodiment, the plurality of insertion portions 16c include first and second insertion portions 16c that are located adjacent to each other and have different heights. Placing the insertion portions 16c with different heights adjacent to each other more effectively reduces the wear of the insertion portions 16c (through holes 16d) and hence reduces short circuits of the metal terminals 17.

[3] In the embodiment, the ceramic housing 16 has an end surface 16e, and the plurality of insertion portions 16c are arranged at the end surface 16e. The plurality of insertion portions 16c can then be provided at the end surface 16e easily.

[4] In the embodiment, at least one of the plurality of insertion portions 16c may have substantially the same height as the end surface 16e, or may protrude or be recessed from the end surface 16e. That is, what is essential is that at least one of the plurality of insertion portions 16c have a different height from other insertion portions 16c, irrespective of whether it has substantially the same height as, or protrudes or is recessed from the end surface 16e.

[5] In the embodiment, a difference Δh (=|h1−h0|) between a height h1 of at least one of the plurality of insertion portions 16c and a height h0 of other insertion portions 16c is from 0.3 to 10.0 mm.

In the embodiments described above, the sensor element 12 is configured to detect NOx concentration in the measured gas, but the sensor element 12 is not limited to the embodiments as long as it is configured to detect the concentration of a particular gas in the measured gas. For example, the sensor element 12 may be adapted to detect oxygen concentration in the measured gas.

When implementing the present invention, various units to improve reliability as an automotive component may be provided without departing from the idea of the present invention.

What is claimed is:

1. A gas sensor comprising:
a sensor element;
an elastic insulating member;
a plurality of lead wires inserted in the elastic insulating member;
a plurality of metal terminals each having a first end electrically connected to the sensor element, and a second end electrically connected to a corresponding one of the plurality of lead wires; and
a ceramic housing including a plurality of ceramic insertion portions each including a through hole in which a corresponding one of the plurality of metal terminals is inserted, wherein each through hole has a smaller diameter than each corresponding ceramic insertion portion, and wherein at least one of the plurality of ceramic insertion portions has a different height from another of the plurality of ceramic insertion portions,
wherein the ceramic housing has an end surface, and the plurality of ceramic insertion portions are arranged at the end surface,
wherein a top surface of at least one of the plurality of ceramic insertion portions protrudes from the end surface toward the elastic insulating member, and wherein a top surface of at least one of the plurality of ceramic insertion portions is recessed from the end surface with respect to the elastic insulating member.

2. The gas sensor according to claim 1, wherein the plurality of ceramic insertion portions include first and second ceramic insertion portions that are located adjacent to each other and have top surfaces of different heights.

3. The gas sensor according to claim 1,
wherein the plurality of ceramic insertion portions are formed in at least two separate groups including a first group of two or more ceramic insertion portions and a second group of two or more different ceramic insertion portions, and
wherein a distance between adjacent ceramic insertion portions within the first group and second group is less than a distance between a first ceramic insertion portion at an end of the first group and a second ceramic insertion portion of the second group that is closest to the first ceramic insertion portion.

* * * * *